United States Patent [19]

Hsu

[11] 4,313,878
[45] Feb. 2, 1982

[54] 4-SUBSTITUTED PHENYL 4'-(5-N-ALKYL-1,3-DIOXAN-2-YL)BENZOATES

[75] Inventor: Ying Y. Hsu, Los Altos, Calif.

[73] Assignee: Timex Corporation, Waterbury, Conn.

[21] Appl. No.: 212,303

[22] Filed: Dec. 3, 1980

[51] Int. Cl.³ .......................................... C07D 319/04
[52] U.S. Cl. ............................ 260/340.7; 252/299.61
[58] Field of Search ....................................... 260/340.7

[56] References Cited

U.S. PATENT DOCUMENTS

| | | | |
|---|---|---|---|
| 4,085,222 | 4/1978 | Rhodes et al. | 424/278 |
| 4,200,580 | 4/1980 | Hsu | 260/340.7 |
| 4,229,315 | 10/1980 | Krause et al. | 252/299 |

FOREIGN PATENT DOCUMENTS

| | | |
|---|---|---|
| 139852 | 1/1980 | German Democratic Rep. |
| 139867 | 1/1980 | German Democratic Rep. |
| 481604 | 11/1975 | U.S.S.R. |

Primary Examiner—Ethel G. Love
Attorney, Agent, or Firm—William C. Crutcher; Edward J. Timmer

[57] ABSTRACT

Disclosed are compounds of the formula:

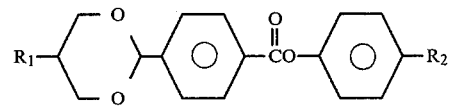

wherein $R_1$ is an alkyl group and $R_2$ is an alkyl, alkoxy, acyloxy, alkyl carbonato group having 1 to 10 carbon atoms, CN or $NO_2$. The compounds of the invention are useful as liquid crystal materials in electrooptical displays.

Also disclosed are novel admixtures of the above benzoate compounds with cyanophenyl dioxane compounds, these admixtures being especially useful for multiplexed electrooptical displays. Preferred admixtures include at least about 40 weight percent of the above benzoate compounds and at least about 40 weight percent of cyanophenyl dioxane compounds with other liquid crystalline compounds such as phenyl cyclohexanecarboxylate, biphenyl and/or phenyl benzoate liquid crystalline compounds also being present in amounts up to about 20 weight percent.

6 Claims, No Drawings

4-SUBSTITUTED PHENYL 4'-(5-N-ALKYL-1,3-DIOXAN-2-YL)BENZOATES

FIELD OF THE INVENTION

The present invention relates to liquid crystal compounds and mixtures thereof which are suitable for use in electrooptical displays, especially of the multiplexed type.

BACKGROUND OF THE INVENTION

It is known to use nematic liquid crystal compounds in electroptic displays. Such displays can be of various types such as the so-called twisted nematic display and multiplexed display and are utilized in constantly increasing numbers in watches and other instruments. Such displays are well known to those skilled in the art.

One of the problems encountered in the utilization of nematic liquid crystal materials in such displays is the availability of stable low viscosity nematic compounds which are liquid at near room temperature and have relatively low transition temperatures to make them practical for use in electro-optic display devices, Further, it is desirable that the nematic liquid crystal material require the application of a minimal amount of electrical potential to obtain the desired effect in order to minimize the power requirements in the display device. Only a limited number of nematic liquid crystal compounds thus far known possess these desired characteristics.

Two compounds possessing the aforementioned combination of properties are described more fully in U.S. Pat. No. 4,200,580 issued Apr. 29, 1980 and in copending U.S. application Ser. No. 135,855 filed Apr. 13, 1980 of common assignee herewith. Those compounds are represented generally by the formula:

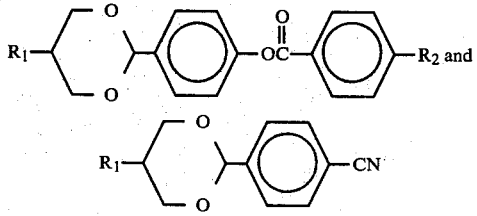

Published Japanese patent application No. 55-85583 (published June 27, 1980) and published U.K. patent application No. 2,041,354A (published Sept. 10, 1980) disclose dioxane compounds having the formula:

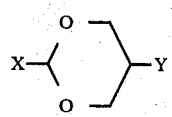

where X and Y can be a variety of substituents.

Although various liquid crystal admixtures have been developed by prior art workers for twisted nematic and multiplexed displays, there still remains the need for new compounds and admixtures with improved properties for optimum display operation.

SUMMARY OF THE INVENTION

According to the present invention there is provided a new group of compounds which are stable liquid crystal materials having a dioxane moiety in aromatic ester molecules. New liquid crystal admixtures containing these compounds are also provided for multiplexing or low voltage electrooptical displays.

The compounds of the present invention are of the formula:

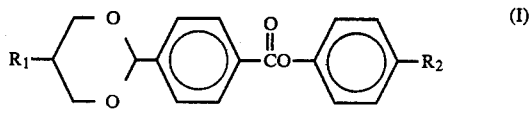

where $R_1$ is an alkyl group, preferably a straight chain of 1 to 10 carbon atoms, and $R_2$ is an alkyl, alkoxy, acyloxy, alkyl carbonato group having 1 to 10 carbon atoms, CN or $NO_2$.

The compounds of the invention are characterized by a broad nematic temperature range, low melting points and low temperature dependence and are preferably present in liquid crystal admixtures in amounts of at least about 40 weight percent.

Liquid crystal admixtures of the invention include compound I and cyanophenyl dioxane, preferably in equal amounts, particularly at least about 40 weight percent of each and are especially useful in multiplexed electrooptical displays. Preferred admixtures also include phenyl cyclohexanecarboxylate, biphenyl and/or phenyl benzoate liquid crystal compounds in amounts up to about 20 weight percent.

The compounds of the invention can be prepared by at least two methods:

METHOD I

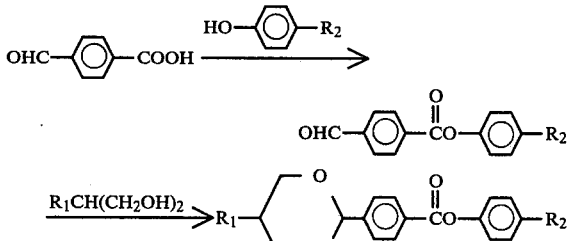

METHOD II

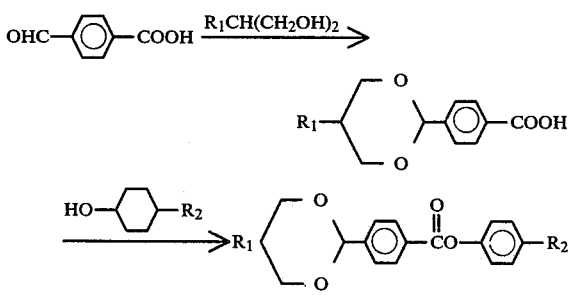

In the foregoing syntheses, $R_1$ and $R_2$ have the same meaning as previously described.

The compounds of the invention are obtained as two isomers. Since the trans configuration is elongated, it presumably is the one which accounts for their liquid crystalline characteristics.

The nature of the invention may be better understood by the following representative embodiments which are included to illustrate the nature of the invention without limiting its scope which is defined in the claims.

DESCRIPTION OF SPECIFIC EMBODIMENTS

EXAMPLE 1

4-n-Butylphenyl 4'-(5-n-butyl-1,3-dioxan-2-yl) benzoate

According to Method I 4-n-Butylphenyl 4'-formylbenzoate

N,N'-dicyclohexylcarbordiimide (54.8 g, 0.266 m) was added to a stirred solution of 4-carboxybenzaldehyde (39 g, 0.26 m), 4-n-butylphenol (40 g, 0.266 m), 4-dimethylaminopyridine (1.2 g) in N,N-dimethylformamide (250 ml) at 0° C. After completion of addition, stirring was continued for one hour at 0° C. and four hours at 20° C. Then methylene chloride (300 ml) was added to the reaction mixture. The precipitated urea was filtered off and the filtrate was washed with 0.5 N HCl, saturated NaHCO₃ solution and water, then dried over sodium sulfate. The resulting solution was eluted through a silica gel column using methylene chloride as solvent. The portions showing a single peak on gas chromatogram were collected. The solvent was evaporated and the residue was crystallized from ethanol to yield 4-n-butylphenyl 4'-formylbenzoate (35.5 g, 47%), mp 60.7° C.

4-n-Butylphenyl 4'-(5-n-butyl-1,3-dioxan-2-yl) benzoate

A mixture of 2-n-butylpropane-1,3-diol (2.64 g, 0.02 m), 4-n-butylphenyl 4'-formylbenzoate (5.64 g, 0.02 m), benezene (100 ml) and a catalytic amount of 4-toluensulfonic acid was azeotropically refluxed until no more water was collected. The cold reaction mixture was washed with saturated NaHCO₃ solution, water and dried over anhydrous sodium sulfate. The solvent was evaporated and the residue was purified by using silica gel column and hexane-methylene chloride as solvent. The solvent was evaporated and the residue was crystallized from ethanol to yield 4-n-butylphenyl 4-(5-n-butyl-1,3-dioxan-2-yl) benzoate (3.8 g, 42%)

CN 75.5° C.

NI 162.4° C.

EXAMPLE 2

4-Cyanophenyl 4'-(5-n-pentyl-1, 3-dioxan-2-yl) benzoate

According to Method II 4-(5-n-Pentyl-1, 3-dioxan-2-yl) benzoic acid

A mixture of 2-n-pentylpropane-1, 3-diol (8 g, 0.054 m), 4-carboxybenzaldehyde (8 g, 0.053 m), benzene (200 ml) and a catalytic amount of 4-toluenesulfonic acid was azeotropically refluxed until no more water was collected. The cold reaction mixture was washed with saturated NaHCO₃ solution and water and then dried over anhydrous sodium sulfate. The solvent was evaporated and the residue was crystallized from ethanol to yield 4-(5-n-pentyl-1, 3-dioxan-2-yl) benzoic acid (12 g, 80%)

CN 213° C.

NI 219° C.

4-Cyanophenyl 4-(5-n-pentyl-1, 3-dioxan-2-yl) benzoate

N,N'-dicyclohexylcarbordiimide (4.12 g, 0.02 m) was added to a stirred solution of 4-(5-n-pentyl-1, 3-dioxan-2-yl) benzoic acid (5.56 g, 0.02 m), 4-cyanophenol (2.6 g, 0.022 m), 4-dimethylaminopyridine (0.2 g) in N,N-dimethylformamide (30 ml) at 0° C. Stirring was continued for one hour at 0° C. and four hours at 20° C., then methylene chloride (50 ml) was added to the reaction mixture. The precipitated urea was filtered off and the filtrate was washed with 0.5 N HCl, saturated NaHCO₃ solution and water, then dried over sodium sulfate. The resulting solution was eluted through a silica gel column using methylene chloride as solvent. The portions showing a single spot on thin layer chromatogram were collected. The solvent was evaporated and the residue was crystallized from ethanol to yield 4-cyanophenyl 4-(5-n-pentyl-1,3-dioxan-2-yl) benzoate (3.3 g, 44%).

CN 138.3° C.

NI 231° C.

Additional examples of compounds of the invention, along with their transition temperatures are given in Table I.

TABLE I

Phase Transition Temperature for
4-Substituted phenyl 4'-(5-n-alkyl-1,3-dioxan-2-yl) benzoate

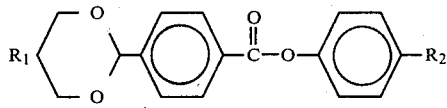

| Compound | R₁ | R₂ | Transition Temperature, °C. | | |
|---|---|---|---|---|---|
| | | | CN(CS) | SN | NI |
| 1 | C₃H₇ | C₃H₇ | 85.0 | | 188.0 |
| 2 | C₃H₇ | C₄H₉ | 68.0 | | 173.0 |
| 3 | C₃H₇ | C₅H₁₁ | 63.3 | | 174.3 |
| 4 | C₃H₇ | C₆H₁₃ | 65.5 | | 161.1 |
| 5 | C₃H₇ | C₇H₁₅ | 60.0 | | 159.1 |
| 6 | C₄H₉ | C₃H₇ | 80.0 | | 178.0 |
| 7 | C₄H₉ | C₄H₉ | 75.5 | | 162.4 |
| 8 | C₅H₁₁ | C₃H₇ | (79.5) | 91.0 | 175.0 |
| 9 | C₅H₁₁ | OC₄H₉ | 85.6 | | 192.0 |
| 10 | C₇H₁₅ | C₂H₅ | (63.0) | 118.3 | 153.8 |
| 11 | C₇H₁₅ | C₃H₇ | (75.9) | 121.0 | 162.0 |
| 12 | C₃H₇ | CN | 164.0 | | 234.5 |
| 13 | C₄H₉ | CN | 147.4 | | 217.0 |
| 14 | C₅H₁₁ | CN | 138.3 | | 231.0 |
| 15 | C₃H₇ | NO₂ | 160.0 | | 206.0 |

(CN = crystal to nematic,
NI = nematic to isotropic liquid,
CS = crystal to smectic and
SN = smectic to nematic)

In addition to having a broad temperature range and relatively low melting points, the compounds of the invention when mixed with cyanophenyl dioxanes and phenyl cyclohexanecarboxylates, biphenyls or phenyl benzoates are especially preferred for multiplexible electro-optic displays. For example, the following admixture for a multiplexible display has been prepared:

EXAMPLE 1

2-(4-Cyanophenyl)-5-n-butyl-1,3-dioxane: 50.77 mole % (40 wt. %)

4-n-Pentylphenyl 4'-(5-n-propyl-1,3-dioxan-2-yl) benzoate: 15.73 mole % (20 wt. %)

4-n-Heptylphenyl 4'-(5-n-propyl-1,3-dioxan-2-yl) benzoate: 14.65 mole % (20 wt. %)

4-n-Heptylphenyl 4'-ethylcyclohexanecarboxylate: 18.85 mole % (20 wt. %)

cholesteryl nonanoate: 0.1 mole %

This mixture exhibited a crystal-nematic temperature (CN) of −4° C. and a nematic-isotropic temperature (NI) of 79.8° C. The electrooptic characteristics of this mixture filled in 10 micron thick cell with low tilt angle are as follows:

10% saturation voltage (V₁₀): 1.72 Volt

90% saturation voltage (V₉₀): 2.30 Volt

Response time (on): 31 ms

Response time (off): 95 ms

EXAMPLE 2

2-(4-Cyanophenyl)-5-n-butyl-1,3-dioxane: 56.95 mole % (45 wt. %)
4-n-Pentylphenyl 4'-(5-n-propyl-1,3-dioxan-2-yl) benzoate: 17.60 mole % (22.5 wt. %)
4-n-Heptylphenyl 4'-(5-n-propyl-1,3-dioxan-2-yl) benzoate: 16.45 mole % (22.5 wt. %)
4-n-Heptylphenyl 4'-n-propylcyclohexanecarboxylate: 9.00 mole % (10 wt. %)
CN −4° C.; NI 90.5° C.
$V_{10}$ 1.70 Volt; $V_{90}$ 2.3 Volt

EXAMPLE 3

2-(4-Cyanophenyl)-5-n-butyl-1,3-dioxane: 47.85 mole % (40 wt. %)
4-n-Pentylphenyl 4'-(5-n-propyl-1,3-dioxan-2-yl) benzoate: 14.80 mole % (20 wt. %)
4-n-Heptylphenyl 4'-(5-n-propyl-1,3-dioxan-2-yl) benzoate: 13.80 mole % (20 wt. %)
4-Cyano-4'-n-pentylbiphenyl: 23.55 mole % (20 wt. %)
CN −6° C.; NI 86.2° C.
$V_{10}$ 1.7 Volt; $V_{90}$ 2.6 Volt

EXAMPLE 4

2-(4-Cyanophenyl)-5-n-butyl-1,3-dioxane: 62.55 mole % (50 wt. %)
4-n-Pentylphenyl 4'-(5-n-propyl-1,3-dioxan-2-yl) benzoate: 19.35 mole % (25 wt. %)
4-n-Heptylphenyl 4'-(5-n-propyl-1,3-dioxan-2-yl) benzoate: 18.10 mole % (25 wt. %)
CN −2° C.; NI 98° C.
$V_{10}$ 1.5 Volt; $V_{90}$ 2.0 Volt

EXAMPLE 5

2-(4-Cyanophenyl)-5-n-butyl-1,3-dioxane: 51.28 mole % (40 wt. %)
4-n-Pentylphenyl 4'-(5-n-propyl-1,3-dioxan-2-yl) benzoate: 15.88 mole % (20 wt. %)
4-n-Heptylphenyl 4'-(5-n-propyl-1,3-dioxan-2-yl) benzoate: 14.80 mole % (20 wt. %)
4-n-Pentylphenyl 4'-n-pentylbenzoate: 18.04 mole % (20 wt. %)
CN −3° C.; NI 80° C.

The general class of biphenyl compounds useful in admixtures of the invention has the general formula

and are described more fully in the Gray et. al., U.S. Pat. No. 3,947,375 issued Mar. 30, 1976. The general class of useful phenyl benzoates has the general formula

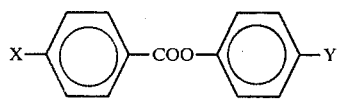

and are described more fully in Steinstrasser U.S. Pat. No. 4,011,137 issued Jan. 4, 1977 and U.S. Pat. No. 4,002,670 issued Jan. 1, 1977.

The general class of cyanophenyl dioxanes useful in admixtures of the invention has the general formula

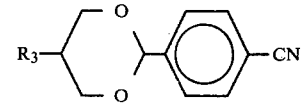

where $R_3$ is typically alkyl or alkoxy. An exemplary synthesis of 2-(4-cyanophenyl)-5-n-butyl-1,3-dioxane employed in Examples 1 through 5 is as follows:

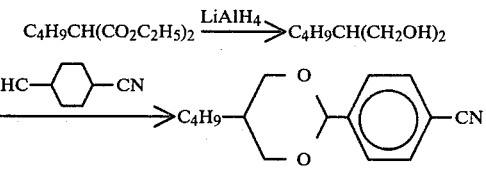

These cyanophenyl dioxanes are claimed in copending U.S. application Ser. No. 136,855 filed Apr. 3, 1980.

The general class of useful phenyl cyclohexanecarboxylates has the general formula

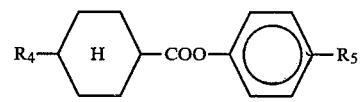

where $R_4$ is typically alkyl or alkoxy and $R_5$ is typically alkyl, alkoxy or cyano. Synthesis of these compounds where $R_4$ is ethyl (Example 1) or propyl (Example 2) and $R_5$ is heptyl is as follows:

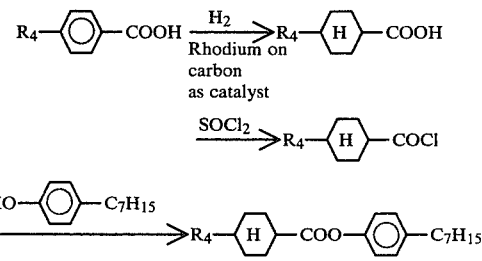

The phenyl cyclohexanecarboxylates are described in East German Pat. Nos. 105,701 and 132,591.

I claim:
1. A compound of the formula:

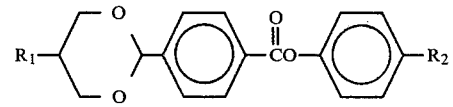

where $R_1$ is an alkyl group and $R_2$ is an alkyl, alkoxy, acyloxy, alkyl carbonato group having 1 to 10 carbon atoms, CN or $NO_2$.
2. A liquid crystal compound of the formula:

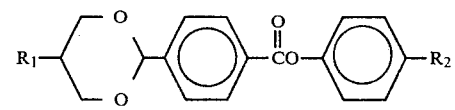

where $R_1$ is a straight chain alkyl group having 1 to 10 carbon atoms, and $R_2$ is an alkyl, alkoxy, acyloxy, alkyl carbonato group having 1 to 10 carbon atoms, CN or $NO_2$.

3. A liquid crystal compound having the formula:

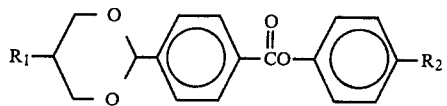

where $R_1$ and $R_2$ can be the same or different alkyl group.

4. The liquid crystal compound of claim 3 where $R_1$ and $R_2$ can be the same or different straight chain alkyl group.

5. The liquid crystal compound of claim 4 wherein $R_1$ is propyl and $R_2$ is pentyl.

6. The liquid crystal compound of claim 4 wherein $R_1$ is propyl and $R_2$ is heptyl.

* * * * *